(12) United States Patent
Terstappen et al.

(10) Patent No.: US 6,623,983 B1
(45) Date of Patent: Sep. 23, 2003

(54) APPARATUS AND METHODS FOR CAPTURE AND ANALYSIS OF PARTICULATE ENTITIES

(75) Inventors: Leon W. M. M. Terstappen, Huntington Valley, PA (US); Galla C. Rao, Princeton Jct., NJ (US)

(73) Assignee: Immunivest Corporation, Wilmington, DE (US)

( * ) Notice: Subject to any disclaimer, the term of this patent is extended or adjusted under 35 U.S.C. 154(b) by 0 days.

(21) Appl. No.: 09/381,795

(22) PCT Filed: Mar. 24, 1998

(86) PCT No.: PCT/US98/05911

§ 371 (c)(1),
(2), (4) Date: Sep. 23, 1999

(87) PCT Pub. No.: WO98/43067

PCT Pub. Date: Oct. 1, 1998

Related U.S. Application Data

(60) Provisional application No. 60/041,460, filed on Mar. 25, 1997.

(51) Int. Cl.[7] ............................................. G01N 33/553
(52) U.S. Cl. .................. 436/526; 436/518; 436/523; 436/525; 436/532; 436/538; 436/501; 436/823; 436/807; 436/824; 435/5; 435/6; 435/7.1; 435/7.25; 435/7.9; 435/91.2; 435/261; 209/214; 209/217; 209/223.1; 209/232; 210/94; 210/95; 210/222; 210/223; 210/695; 536/24.3
(58) Field of Search ................................. 436/526, 518, 436/523, 525, 532, 538, 501, 823, 807, 824; 435/6, 5, 7.1, 7.25, 7.9, 91.2, 261; 209/214, 217, 223.1, 232; 536/24.3; 210/94, 95, 222, 223, 695

(56) References Cited

U.S. PATENT DOCUMENTS

| | | | | |
|---|---|---|---|---|
| 4,230,685 A | * | 10/1980 | Senyei et al. | 424/12 |
| 5,081,030 A | * | 1/1992 | Civin | 435/240.2 |
| 5,108,933 A | * | 4/1992 | Liberti et al. | 436/501 |
| 5,158,871 A | * | 10/1992 | Rossomando et al. | 435/7.32 |
| 5,186,827 A | * | 2/1993 | Liberti et al. | 210/222 |
| 5,200,084 A | * | 4/1993 | Liberti et al. | 210/695 |
| 5,466,574 A | * | 11/1995 | Liberti et al. | 435/5 |
| 5,508,164 A | * | 4/1996 | Kausch et al. | 435/6 |
| 5,514,340 A | * | 5/1996 | Lansdorp et al. | 422/101 |
| 5,541,072 A | * | 7/1996 | Wang et al. | 435/7.21 |
| 5,558,839 A | * | 9/1996 | Matte et al. | 422/101 |
| 5,622,831 A | * | 4/1997 | Liberti et al. | 435/7.21 |
| 5,646,001 A | * | 7/1997 | Terstappen et al. | 435/7.21 |
| 5,660,990 A | * | 8/1997 | Rao et al. | 435/6 |
| 5,670,381 A | | 9/1997 | Jou et al. | |
| 5,691,208 A | | 11/1997 | Mitenyi et al. | |
| 5,698,271 A | * | 12/1997 | Liberti et al. | 427/550 |

(List continued on next page.)

FOREIGN PATENT DOCUMENTS

| | | |
|---|---|---|
| DE | 19501916 | 1/1994 |
| GB | 2300258 | 10/1996 |
| WO | 9411078 | 5/1994 |
| WO | 9415696 | 7/1994 |
| WO | 9607913 | 3/1996 |
| WO | 9627132 | 9/1996 |

*Primary Examiner*—Christopher L. Chin
*Assistant Examiner*—Pensee T. Do
(74) *Attorney, Agent, or Firm*—Dann Dorfman Herrell and Skillman

(57) ABSTRACT

Apparatus and methods are disclosed which facilitate immobilization of magnetically labelled particulate entities, e.g., cells, preferably in a defined pattern, on a collection surface via binding between specific binding pair members, as an aid to particle analysis.

14 Claims, 3 Drawing Sheets

U.S. PATENT DOCUMENTS

| | | | |
|---|---|---|---|
| 5,736,413 A | | 4/1998 | Uzan et al. |
| 5,741,714 A | | 4/1998 | Liberti |
| 5,763,203 A | * | 6/1998 | Ugelstad et al. ............ 435/7.24 |
| 5,795,470 A | * | 8/1998 | Wang et al. ................. 210/222 |
| 5,851,770 A | * | 12/1998 | Babon et al. ................... 435/6 |
| 5,876,593 A | * | 3/1999 | Liberti et al. .................. 210/95 |
| 5,925,573 A | * | 7/1999 | Colin et al. ................... 436/525 |
| 5,993,665 A | * | 11/1999 | Terstappen et al. ......... 210/695 |
| 6,013,532 A | * | 1/2000 | Liberti et al. ................ 436/526 |
| 6,078,782 A | * | 6/2000 | Leland et al. ................. 435/7.1 |

\* cited by examiner

APPARATUS AND METHODS FOR CAPTURE AND ANALYSIS OF PARTICULATE ENTITIES

This application is U.S. National Stage of PCT/US98/05911, which claims the benefit of U.S. Provisional Application No. 60/041,460, filed Mar. 25, 1997.

FIELD OF THE INVENTION

This invention relates to apparatus and methods for the enumeration, examination, and manipulation of magnetically labeled particulate entities, and especially biological particles, such as cells.

BACKGROUND OF THE INVENTION

A magnetic material or magnetic dipole will move in a magnetic field gradient in the direction of increasing magnetic field strength. Magnetic gradients employed in fluid separations are broadly divided into two categories. Internal magnetic gradients are formed by inducing magnetization in a susceptible material placed in the interior of a separation vessel. External gradients are formed by an externally positioned magnetic circuit.

In the case of a simple rectangular bar magnet, for example, field lines which form magnetic circuits conventionally move from North to South and are easily visualized with iron filings. From this familiar experiment in elementary physics it will be recalled that there is greater intensity of field lines nearest the poles. At the poles, the edges formed at the intersections of the sides and faces of the bar will display an even greater density or gradient. Thus, a steel ball placed near a bar magnet is first attracted to the nearest pole and next moves to the region of highest field strength, typically the closest edge. For magnetic circuits, any configuration which promotes increased or decreased density of field lines will generate a gradient. In opposing magnet designs, such as N-S-N-S quadrupole arrangements, opposing North poles or opposing South poles will have field lines such that in the center of such an arrangement there will be zero field. From the circuits that result from a North pole being opposite to each adjacent South pole, such arrangements generate radial magnetic gradients.

Internal high gradient magnetic separators have been employed for nearly 50 years for removing weakly magnetic materials from slurries such as in the kaolin industry, or for removing nanosized magnetic materials from solution. (See Kolm, Scientific American, November 1975). In an internal high gradient magnetic separator, a separation vessel is positioned in a uniform magnetic field. A ferromagnetic structure is positioned within the vessel in order to distort the magnetic field and to generate an "internal" gradient in the field. Typically, magnetic grade stainless steel wool is packed in a column which is then placed in a uniform magnetic field which induces gradients on the steel wool as in U.S. Pat. No. 3,676,337 to Kolm. Gradients as high as 200 kGauss/cm are easily achieved. The magnitude of the field gradient in the vicinity of a wire is inversely related to the wire diameter. The spatial extent of the high gradient region is proportionally related to the diameter of the wire. As will be explained below, collection of magnetic material takes place along the sides of the wire, perpendicular to the applied magnet field lines, but not on the sides tangent to the applied field. In using such a system, material to be separated is passed through the resulting magnetic "filter". Then, the collected material is washed, and the vessel is moved to a position outside the field where magnetic materials are removed, allowing the collector to be reused.

Various attempts have been made to perform continuous (non-cycle) high gradient magnetic separation. Improvements include flow-through devices with fluctuating fields to separate magnetic material from non-magnetic material, as in U.S. Pat. No. 3,902,994 to Maxwell. Removable screens of ferromagnetic material are also well known in the art as in U.S. Pat. No. 4,209,394 to Kelland. Other flow-through devices are described in U.S. Pat. Nos. 4,261,815 and 4,663,029 to Kelland, U.S. Pat. No. 4,526,681 to Friedlaender, et al., and commonly owned U.S. patent application Ser. Nos. 08/424,271 and 08/482,652.

A method and apparatus for separating cells and other fragile particles is described by Graham, et al in U.S. Pat. No. 4,664,796. The apparatus contains a rectangular chamber within a cylinder. One pair of opposing sides of the chamber are made of non-magnetic material, while the other sides are made of magnetic material. The flow chamber is packed with a magnetically responsive interstitial separation matrix of steel wool. The material to be separated is passed through the chamber, which is positioned in a uniform magnetic field. During separation, the chamber is aligned in the magnetic field such that the magnetic sides of the chamber are parallel to the applied field lines, thus inducing a high gradient about the interstitial matrix in the chamber. When the chamber is in this position, magnetically labeled cells are attracted to the matrix and held thereon, while the non-magnetic components are eluted. The chamber is then rotated, so that the magnetic sides face magnets, which "shunts" or "short-circuits" the magnetic field, reclines the gradients in the flow chamber, and allows the particles of interest to be removed by the shearing force of the fluid flow.

Other internal magnetic separation devices are known. Commonly owned U.S. Pat. No. 5,200,084 discloses the use of thin ferromagnetic wires to collect magnetically labeled cells from solution. U.S. Pat. No. 5,411,863 to Miltenyi discloses the use of coated steel wool, or other magnetically susceptible material to separate cells. U.S. patent application Ser. No. 08/424,271 by Liberti and Wang discloses an internal HGMS device useful for the immobilization, observation, and performance of sequential reactions involving cells.

Turning to the magnetic particles used in such collection devices, over the last twenty years, superparamagnetic materials have become the backbone of magnetic separations technology in a variety of healthcare and bioprocessing applications. Such materials, ranging in size from 25 nm to 100 $\mu$m, are characterized in that they are only magnetic when placed in a magnetic field. Once the field is removed, they cease to be magnetic and can normally easily be dispersed into suspension. The basis for superparamagnetic behavior is that such materials contain magnetic cores smaller than 20–25 nm in diameter, which is estimated to be less than the size of a magnetic domain. A magnetic domain is the smallest volume in which a permanent magnetic dipole exists. Magnetically responsive particles can be formed about one or more such cores. The magnetic material of choice is magnetite, although other transition element oxides and mixtures thereof having appropriate particle size exhibit such superparamagnetic behavior.

Magnetic particles of the type described above have been used for various applications, particularly in health care, e.g. immunoassay, cell separation and molecular biology. Particles ranging from 2 $\mu$m to 5 $\mu$m are commercially available from Dynal. These particles are composed of spherical polymeric materials into which magnetic crystallites have been deposited. These particles because of their magnetite content and size, are readily separated in relatively low external gradients (0.5 to 2 kGauss/cm). Another similar class of materials are particles manufactured by Rhone Poulenc which typically are produced in the 0.75 µm range. Because of their size, they separate more slowly than the Dynal beads in equivalent gradients. Another class of particulate magnetic material is available from Advanced Magnetics. These particles are basically clusters of magnetite crystals, about 1 µm in size, which are coated with amino polymer silane to which bioreceptors can be coupled. These highly magnetic materials are easily separated in gradients as low as 0.5 kGauss/cm. Due to their size, both the Advanced Magnetics and Rhone Poulenc materials remain suspended in solution for hours at a time.

There is a class of magnetic particles which has been applied to bioseparations and which have characteristics which place them in a distinct category from those described above. These are nanosized colloids (see U.S. Pat. No. 4,452,773 to Molday; U.S. Pat. No. 4,795,698 to Owen, et al; U.S. Pat. No. 4,965,007 to Yudelson; U.S. Pat. No. 5,512,332 to Liberti & Piccoli and U.S. Pat. No. 5,597,531 to Liberti et al.; and U.S. patent application Ser. No. 08/482, 448 of Liberti et al). They are typically composed of single crystal to multi-crystal agglomerates of magnetite coated with polymeric material which make them compatible with aqueous liquids. Individual crystals range in size from 8 to 15 nm. The coatings of these materials have sufficient interaction with solvent water to keep them permanently in a colloidal suspension. Typically, well coated particles below 150 nm will show no evidence of settling for as long as 6 months. These materials have substantially all the properties of ferrofluids.

Because of the particle size and strong interaction with solvent water, substantial magnetic gradients are required to separate ferrofluids. It had been customary in the literature to use steel wool column arrangements, such as described above, which generate 100–200 kGauss/cm gradients. However, it was subsequently observed that such materials form "chains" (like beads on a string) in magnetic fields, thus allowing separation in gradient fields as low as 5 or 10 kGauss/cm. This observation led to development of separation devices using large gauge wires which generate relatively low gradients. Large gauge wires can be used to cause ferrofluids to produce uniform layers upon collection. By controlling amounts of ferrofluid in a system, a monolayer can be formed. Magnetically labeled cells can thus be made to form monolayers as described in commonly owned U.S. Pat. Nos. 5,186,827 and 5,466,574.

Analysis of the cellular composition of biological fluids is used in the diagnosis of a variety of diseases. Microscopic examination of cells smeared or deposited on slides and cytochemically stained has been the traditional method for cell analysis. Introduction of impedance based cell counters in the late 1950's has led to a major advance in the accuracy of cell enumeration and cell differentiation. Since then various other technologies have been introduced for cell enumeration and differentiation such as Flowcytometry, Fluorescence Activated Cell Sorting, Quantitative Buffy Coat Analysis, Volumetric Capillary Cytometry, Laser Scanning Cytometry and various image analysis systems. Fluorescence based flowcytometry has dramatically improved the ability to discern different cell types in heterogeneous cell mixtures. This technique is commonly used, for example, to measure the absolute and relative number of cells in a specific subset of leukocytes in blood. In practice, a blood sample is drawn and incubated with a fluorescently labeled antibody specific for this subset. The sample is then diluted with a lysing buffer, optionally including a fixative solution, and the dilute sample is analyzed by flow cytometry. This procedure for analysis can be applied to many different cell surface antigens. Simultaneous assessment of multiple parameters of individual cells which pass the measurement orifice of a flow cytometer at a speed of up to 1,000 to 10,000 cells/sec is indeed a powerful technology. However, there are limitations on this technology, such as the inability to conveniently accommodate high cell concentrations (e.g., blood needs to be diluted), impracticality of the detection of infrequent or rare cells, and the inability to reexamine the cells of interest. In such situations, the time needed for the flow cytometer to analyze these samples becomes extremely long, thus decreasing the sample throughput. In addition, the settling of cells in the sample tube will occur during this time and require continuous mixing of the sample. To overcome these limitations, clinical samples to be analyzed are typically subjected to various enrichment techniques such as erythrocyte lysis, density separation, immunospecific selection or depletion of cell populations prior to analysis by flow cytometry.

Coated surfaces have been used for many research and clinical applications over the last several decades. Coated plates, reaction vessels, and tubes are well-known in the art. Coated surfaces have found particular use in immunoassays, and have seen wide usage since the 1960's, starting with radioimmunoassays. Coated cup assays remain common in many of the clinical analyzers in laboratory use today, such as the VITROS ECI, Cyber-fluor, Delfia and the ES-300 systems. See also U.S. Pat. No. 4,376,110. Advantages of coated cup assays include that they provide a single, essentially homogeneous layer of analyte for analysis, which will withstand vigorous wash steps and result in low non-specific binding.

Commonly owned U.S. patent application Ser. No. 08/516,694 to Rao & Liberti relates to the use of a coated surface combined with a magnetic immunoassay. Magnetically collected material is immobilized on a coated surface through a specific binding pair reaction. The specific binding pair is borne upon the magnetic particle, which results in the non-reorientation of the magnetically collected material, when such particles are perturbed by sample removal or buffer addition and removal. The formation of a monolayer of magnetic material upon the coated surface is also facilitated, which reduces trapping of potentially signal-interfering substances. As a result, resuspension during washing or during signal readout is not required. Additionally, since the binding pair is adhered to the magnetic particle, all magnetic particles become bound to the coated surface, which prevents the loss of particles during washing, resulting in higher signal. However, in the separation of other biological material, such as cells, other concerns must be taken into account. Sample sizes are generally larger than in immunoassay, requiring larger volumes of magnetic material. Additionally, cells are much larger than the analytes in immunoassays, thus requiring larger amounts of magnetic particle reagents in order to convey the cell in the magnetic field. Increased amounts of such reagents are also required to drive the binding reaction, resulting in significant excesses of magnetic material. The sample volume reduction needed to concentrate the cells for analysis also results in an increase in the concentration of magnetic particle reagents. Such a large excess of material tends to obscure the microscopic examination of cells and inhibits their further analysis.

Other cytological techniques involve cell deposition on a slide for microscopic analysis. Sample preparation for these techniques include cell centrifuges, the Cytoshuttle, sorting of cells by Fluorescence Activated Cell Sorting (FACS), or other cytometric techniques by which target cells are separated after analysis/identification, such as B-D's FACS Sort. Cell centrifuges are sold by several companies, including Shandon Lipshaw and StatSpin. In these systems, a centrifuge is used to deposit a cell sample on a microscope slide. However, drawbacks of the system include cell loss in the centrifugation step and the inability to selectively deposit target cells onto a slide. A pre-selection of cells is required in such cases. A pre-selection is also required for the Cytoshuttle, available from Cancer Diagnostics, which uses a filter to collect cells on special filter paper. The cells collected on the filter paper are then transferred to a microscope slide for analysis. Cell loss is also a problem with the Cytoshuttle.

Cell sorting additions to flow cytometers have been sold by Becton-Dickinson (B-D), Coulter, and Ortho. Shapiro's *Practical Flow Cytometry*, (3rd ed. Wiley-Liss, NY, 1995) provides a comprehensive description of the theory behind this apparatus. Basically, there are two types of sorters, droplet and fluidic. The droplet sorters include FACSVantage (B-D), MoFlo (Cytomation) and EPICS (Coulter), which divide the fluid stream into individual charged droplets, some of which contain cells. Charged plates deflect the droplets into one or two streams from which they can be collected. In fluidic sorters, such as the FACS Sort (B-D), a mechanical arm is placed in the fluid stream. When a target cell passes, the arm is extended into the sample stream, capturing the fluid containing the target cell and then moving back to its original position in the fluid stream. Since the arm is placed in the fluid stream, a continuous flow of fluid is collected along with the target cell, resulting in a considerable dilution of the target cells.

The ability to deposit target cells in specific position for analysis has been described by Stovel & Sweet (J Hitochem & Cytochem, 27: 284–288 (1979)) and is commercially available as B-D's Accurate Cell Deposition Unit (ACDU). The ACDU is an option added to a droplet sorter which allows sorting of cells into a microtiter well or onto a microscope slide. The slide is guided via computer control to capture target cells on a pre-defined region of the slide. Thus, one is able to sequester individual cells on a portion of a microscope slide, although it is difficult to maintain cell integrity and morphology. However, in the Stovel & Sweet system, the cells are sorted into individual "splash circles" with a 270 micron diameter, making it relatively difficult to locate a single cell within this large diameter. Additionally, not all cells which fall within the sort gate of the scatterplot are actually deposited on the slide, and it is thus impossible to correlate the individual deposited cells to the cells in the sort gate. This problem has been overcome by adding an additional analysis point to determine if the gated cell was actually successfully sorted. This system has been used to index cells sorted into microtiter wells. See Terstappen et al., "Characterization of Human Primitive Hematopoietic Stem Cells", presented at Joint International Workshop on Foetal and Neonatal Hematopoiesis and Mechanisms of Bone Marrow Failure, Apr. 3–6, 1995, Paris. Despite these features, droplet sorting is inherently more complex than fluidic sorting and such instruments could not practically be used in a clinical setting, even with highly trained technicians.

Fluidic sorters of the type described in U.S. Pat. No. 5,030,002 to North are relatively easy to maintain and operate, but they have their own set of drawbacks. The mechanical arm is positioned in the fluid stream and liquid is continuously collected by the arm. A target cell is caught when the arm moves into the sample stream. The sheath fluid rate thus determines the collection volume. For example, when the contents of a 500 $\mu$l sample has to be sorted, it will take approximately 500 seconds (sample flow 1 $\mu$l/sec.) and will produce a total volume of about 50 ml (sheath fluid rate of 18 ml/min. and catcher arm rate of 6 ml/min.). Irrespective of the number of captured cells, the volume will be approximately 50 ml.

From the foregoing discussion, it will be appreciated that a need exists for apparatus and methods which are capable of efficiently and effectively separating magnetically labeled particles, such as cells, from a fluid medium, including whole blood or sheath fluid, resulting in the capture of the cells of interest in a pre-determined pattern on a non-magnetic capture surface, such as a microscope cover slip.

SUMMARY OF THE INVENTION

The present invention provides apparatus and methods for the collection and immobilization of particulate entities, especially those of biological origin, such as cells.

The particulate entities are labeled with magnetically responsive particle and collected on a collection surface, followed by immobilization on the collection surface as a result of an interaction between the members of a specific binding pair, one member of which is uniformly or non-uniformly affixed to the collection surface, and the other member of which is associated with the particulate entity sought to be immobilized.

In a particularly preferred aspect of the invention, an apparatus is provided for immobilization of magnetically labelled particulate entities on a collection surface via binding between the members of a specific binding pair. In this aspect of the invention, the particulate entities comprise one member of the specific binding pair, with the other member being affixed to at least a portion of the collection surface. The preferred apparatus of the invention comprises magnetic means for providing a magnetic field, a collection surface disposed in the magnetic field generated by the magnetic means, and having affixed thereto the other member of said specific binding, as noted above, and ferromagnetic localization means operably associated with the collection surface for producing a magnetic field gradient having a defined pattern on the portion of the collection surface bearing the other specific binding pair member, whereby the magnetically labelled particulate entities are caused to adhere to the collection surface under the influence of the magnetic field gradient and to become immobilized on the collection surface when subjected to conditions promoting reaction between the specific binding pair members.

As will appear from the following description, the present invention offers a number of notable advantages over existing analytical techniques for separation and analysis of particulate analytes, e.g., cells or microbes, within test samples such as bodily fluids, culture fluids or samples from the environment, which may contain non-magnetic components. One distinct advantage of the present invention is maintenance of the target entities intact and/or viable upon separation to permit analysis, identification, or characterization of the target entities.

DETAILED DESCRIPTION OF THE INVENTION

Figure 1:
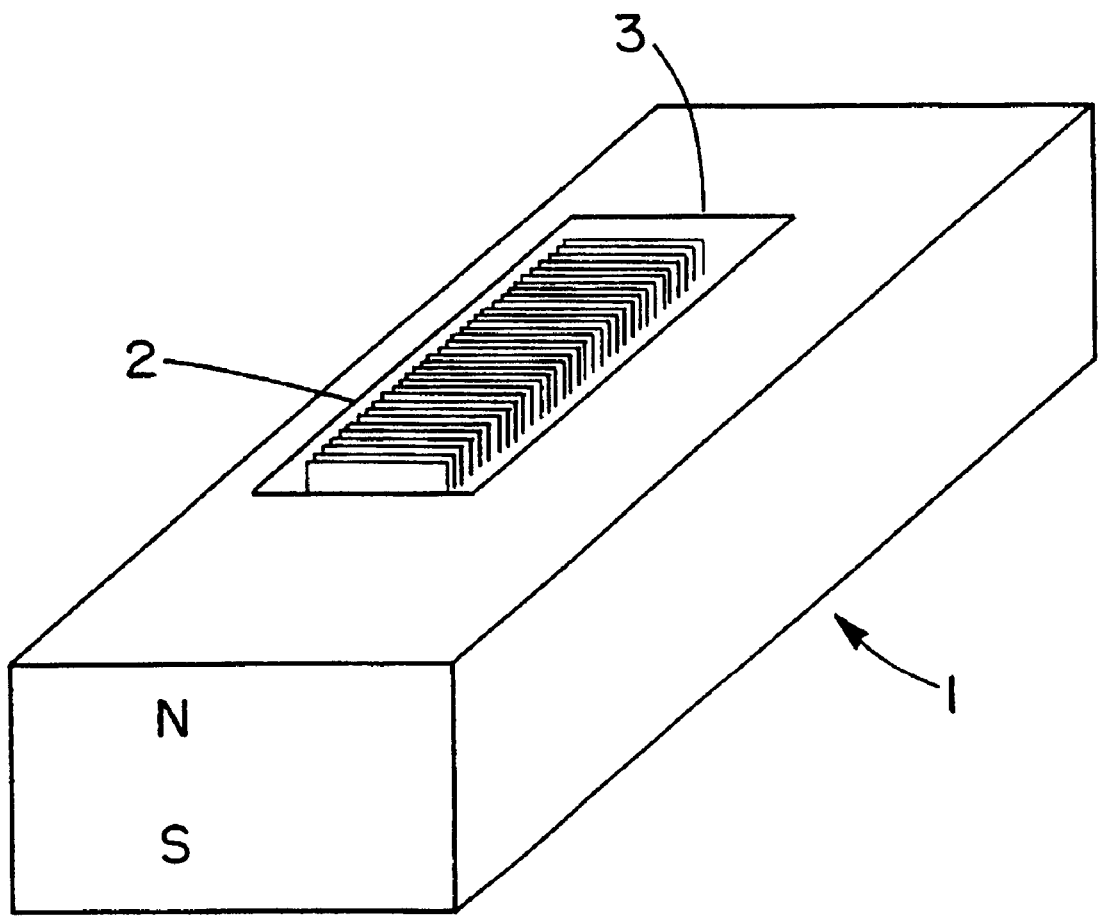
FIG. 1 shows a representative embodiment of the present invention in which a strip of unused staples disposed on a magnet is used as a ferromagnetic cell alignment means.

The instant invention provides for the collection and immobilization of magnetically labeled particulate analyte, such as cells, in a predetermined pattern on a non-magnetic surface. The term "particulate analyte", as used herein, includes a variety of substances of potential biological or medical interest which may be measurable individually or as a group. Representative examples of "particulate analytes" include cells, both eukaryotic (e.g., leukocytes, erythrocytes or fungi) and prokaryotic (e.g., bacteria, protozoa or mycoplasma), viruses, cell components, macromolecules and the like. Often it is desirable to determine the presence or quantity of a particular cell type for diagnostic or therapeutic purposes. Examples include the determination of leukocytes within a population of blood cells, helper T lymphocytes within a population of lymphocytes, fetal cells within maternal circulation, virus-infected cells within a population of uninfected and infected cells, or neoplastic cells within a population of normal and neoplastic cells. Although the method of this invention is useful for the determination of many different types of particulate analyte, it will be exemplified hereinbelow with particular reference to the detection of human blood cells.

The non-magnetic collection surface, preferably a microscope cover slip, is coated with a specific binding substance, that specifically binds a characteristic determinant of the target cells. The collection surface is placed on a magnet and the target cells, which are conveyed to the collection surface under the influence of the magnetic field become immobilized thereon as a result of the binding interaction with the specific receptor for a characteristic cell surface antigen of the target cell, a coating of which receptor is provided on the collection surface. When the surface is removed from the magnetic field, any excess magnetic material, such as magnetic labels that are not bound to specific binding substances affixed to the collection surface, or any non-magnetic substance may be removed from the surface, e.g., by washing. The invention thus allows for the removal of magnetic material not actually bound to target cells, improving the visualization of the target cells by microscopic means and improving conditions for the further culturing or other use of the cells.

In a particularly preferred embodiment of the invention, the collection surface is placed on a magnet which, due to pole piece design or some other magnetic gradient phenomenon, provides a "ferromagnetic localizing means" which causes an ordered arrangement of magnetically labelled cells to form on the collection surface. The target cells may be present in a biological specimen such as whole blood, leukopheresis product, bone marrow, or other bodily fluid, as well as cultured cells. The test sample contains magnetically labeled target cells, as well as excess magnetic particles and, usually, non-target material. When the test sample is placed on the collection surface, the magnetically labeled target cells immediately migrate to the region of the surface in registry with the patterned magnetic field gradient produced by the ferromagnetic localizing means. Thus, the magnetically labelled cells will assume the shape, arrangement, or pattern produced by the ferromagnetic localizing means. The target cells which are magnetically conveyed to the collection surface become immobilized thereon as a result of binding interaction with the specific receptor for a characteristic cell surface antigen of the target cell, a coating of which receptor is provided on the collection surface. When the surface is removed from the magnetic field, any excess magnetic material, such as magnetic labels that are not bound to specific binding substances affixed to the collection surface, or any non-magnetic substance may be removed from the surface, e.g., by washing, leaving a defined pattern of target material immobilized on in a predetermined portion of the collection surface. In embodiments wherein the collection surface is provided by a microscope cover slip and the particulate analyte of interest constitutes cells, staining techniques such as (Immuno) cytochemistry, in situ hybridization, or in situ PCR can be applied to search for the presence or absence of components of interest. The ordered array of cells will greatly facilitate their microscopic examination and reduce the time required to scan the microscope slide for the presence of the cells of interest. The morphology of the cells is retained throughout the entire process.

The term "localization", as used herein, refers to the ordered arrangement of particulate analyte formed on a predetermined portion of a collection surface. The portion of the collection surface on which particle localizing occurs may be a point, a straight or curved line, an ordered array of straight or curved lines, which may be of any desired pattern or shape, subject to the size constraints of the collection surface. The term "ferromagnetic localization means", as used herein, refers to ferromagnetic material which becomes magnetized in the presence of a magnetic field to attract magnetically responsive particles. It may be in the form of wires, spheres, or textured material. Ferromagnetic material includes iron, nickel, cobalt, alloys of the same, alloys of magnetic rare Earth elements, and other extremely paramagnetic materials. It is also possible to create an extremely finely focused magnetic field without the need of pole pieces, as described above. Magnetic design, including opposing magnetic poles held closely together can create high field gradients in tightly defined regions on an adjacent surface. The term "internal gradients", as used herein, refers to magnetic field gradients induced upon susceptible material when placed in a magnetic field. Electro-magnets can also be used to produce magnetic fields useful in practicing the present invention.

The method aspects of the invention have broad utility in the separation of particulate biological entities which include a wide variety of substances of biological origins including cells, both eukaryotic (e.g. leukocytes, erythrocytes, or fungi) and prokaryotic (e.g. bacteria, protozoa or mycoplasma), viruses, cell components, such as organelles, vesicles, endosomes, lysosomal packages or nuclei, as well as molecules (e.g. proteins) and macromolecules (e.g. nucleic acids—RNA and DNA). The biological entities of interest may be present in samples or specimens of varying origins, including, without limitation, biological fluids such as whole blood, serum, plasma, bone marrow, sputum, urine, other bodily fluids, such as cerebrospinal fluid, amniotic fluid or lavage fluids, as well as tissue homogenates, disaggregated tissue, or cell culture medium. They may also be present in material not having a clinical source, such as sludge, slurries, water (e.g. ground water or streams), food products or other sources. The method of the invention also has utility in the separation of various bacteria and parasites from fecal matter, urine, or other sources.

The term "determinant" is used here in a broad sense to denote the molecular contact regions on target substances that are recognized by receptors in specific binding pair reactions. When used in reference to any of the above-referenced biological entities, "determinant" means that portion of the biological entity involved in and responsible for selective binding to a specific binding substance, the presence of which is required for selective binding to occur. The expression "characteristic determinant" is used herein in reference to cells, for example, to signify an epitope (or group of epitopes) that serve to identify a particular cell type and distinguish it from other cell types. Cell-associated determinants include, for example, components of the cell membrane, such as membrane-bound proteins or glycoproteins, including cell surface antigens of either host or viral origin, histocompatibility antigens or membrane receptors.

The expression "specific binding substance" or "specific binding pair" as used herein refers to any substance that selectively recognizes and interacts with the characteristic determinant on a particulate biological entity of interest, to substantial exclusion of determinants present on biological entities that are not of interest. Among the specific binding substances which may be used in affinity binding separations in accordance with this invention are antibodies, anti-haptens, lectins, peptides, peptide-nucleic acid conjugates, nucleic acids, hormones, growth factors and more specifically Protein A, Protein G, concanavalin A and soybean agglutinin. Specific binding substances can also be covalently attached to members of other specific binding pairs, such as biotin, avidin, streptavidin or other common capture agents. It is important to note that the term "specific binding", as used herein, refers to the binding that occurs between specific binding substances and cell subpopulations, on the one hand, and between specific binding substances and cell subsets, on the other hand. For example, CD4 Mab specifically binds a characteristic determinant on the leukocyte subset known as T-cells, whereas CD45 Mab specifically binds to all leukocytes. HLA class I antigens recognize an even broader range of cells beyond the subpopulation of leukocytes. However, all three substances are considered specific binding substances.

The term "antibody" as used herein includes immunoglobulins, monoclonal or polyclonal antibodies, immunoreactive immunoglobulin fragments, single chain antibodies, and peptides, oligonucleotides or any combination thereof which specifically recognize determinants with specificity similar to traditionally generated antibodies.

The term "magnetically responsive particles" as used herein refers to magnetic particles of metallic or organometallic composition, optionally coated with polymer, preferably coated with a polymer of biological origin such as BSA. The particles may be linked with an antibody or other specific binding substance to allow them to specifically bind particulate biological entities of interest. Also included within the ambit of "magnetically responsive particles" are the complexes resulting from the interaction between particulate biological entity and magnetic particle, which may be optionally bound to a fluorescent label or other detectable label. Suitable magnetic material is manufactured by Dynal, Rhone Poulanc, Miltenyi, Cardinal Associates, Bangs Labs, Ferrofluidics, Polysciences, and Immunicon.

The preferred magnetic particles for use in carrying out this invention are particles that behave as true colloids. Such particles are characterized by their sub-micron particle size, which is generally less than about 200 nanometers (nm) (0.20 microns), and their stability to gravitational separation from solution for extended periods of time. Such small particles facilitate observation of the target entities via optical microscopy since the particles are significantly smaller than the wavelength of visible light. Suitable materials are composed of a crystalline core of superparamagnetic material surrounded by molecules which may be physically absorbed or covalently attached to the magnetic core and which confer stabilizing colloidal properties. Most typically, the crystalline core is an agglomeration of single crystals, each sufficiently small that they do not contain a complete magnetic domain. When agglomerated via intercrystalline attractive forces, the magnetic core sizes can be orders of magnitude larger than a magnetic domain, but these materials nonetheless remain superparamagnetic. As a consequence, North Pole, South Pole alignment and subsequent mutual attraction/repulsion of these colloidal magnetic particles does not appear to occur even in moderately strong magnetic fields, contributing to their solution stability. Accordingly, colloidal magnetic particles are not readily separable from solution as such even with powerful electromagnets, but instead require a magnetic gradient to be generated within the test medium in which the particles are suspended in order to achieve separation of the discrete particles. Magnetic particles having the above-described properties can be prepared as described in U.S. Pat. Nos. 4,795,698; 5,512,332; 5,597,531 and U.S. application Ser. No. 08/482,448.

The specimen material used in practicing the instant invention may be any liquid or solution which contains the particulate analyte of interest, and is preferably whole blood. A test sample is incubated with antibodies or other specific binding substances, either directly or indirectly linked to magnetic particles for the time required to allow optimal binding of the substance to its corresponding target particle. Optionally, the specimen material may also be incubated with an enzymatic label, a dye, or other detectable label. In addition, a member of a specific binding pair may optionally be used to label the target material. After the target particles have been labeled with the magnetically responsive material, an optional magnetic collection serves to concentrate the target particles. After magnetic collection, the excess non-magnetic (non-target) component(s) of the test sample is (are) aspirated, and the remaining material may be removed from the magnetic field and resuspended in a substantially smaller volume. After the target particles have been labeled, a signal amplification reagent may optionally be added to increase the signal generated for eventual detection of the target particles. The most common signal amplification reagents are biotinylated antibodies used with streptavidin labeled enzyme, but other such systems are known in the art. As another option, the enzymatic labels, dyes, detection antibodies may be added for later use, or the specific binding pair labels may be added at the time of signal amplification. Finally, the magnetically labeled target particles are placed upon a collection surface for magnetic localization.

The surface used in the practice of the instant invention may be of glass, plastic, quartz, or any other material which permits observation of the target biological material. The substrate which provides the collection surface must be non-magnetic and relatively thin. The thickness of the substrate is chosen in relation to the strength of the magnets and ferromagnetic localization means used. The collection surface-bearing substrate is preferably 0.1–0.3 mm thick. A particularly preferred collection surface-bearing substrate is a glass or plastic microscope cover slip. In some instances, it may be desirable use a containment means, such as a gasket disposed on said collection surface to limit loss of sample, especially in the case of a liquid sample more than about 50 µl. The containment means is preferably non-reactive and non-adherent to the target material. After magnetic collection and immobilization, the gasket, for example, is easily removable to efficiently wash the surface. In other instances, it may be desirable to use a chamber which includes a surface for magnetic collection. It is obvious that only the part of the chamber for the magnetic localization used be suitably thin and compatible for observation of the localized target particles. It will also be appreciated that the test sample can be flowed over the collection surface.

The collection surface is coated with one member of a specific binding pair. Among the specific binding substances which may be used in affinity binding separations are antibodies, anti-haptens, lectins, peptides, peptide-nucleic acid conjugates, nucleic acids, Protein A, Protein G, concanavalin A, soybean agglutinin, hormones, growth factors, avidin, streptavidin, or biotin. Preferred for this purpose are antibodies, which include single chain antibodies and peptides, oligonucleotides or any combination thereof which specifically recognize determinants with specificity similar to traditionally generated antibodies. Particularly preferred are antibodies against cell-surface antigens. The surface may also be coated with a member of a binding pair which inserts into or adheres to a cell membrane via specific chemical reaction with the internal or external aspect of the lipid bilayer such as lipophyllic carbocyanide compounds, aminostyryl compounds, or anti-phosphatidal choline. The surface may also be coated with a substance, such as polylysine, which binds to all cells based on charge.

The collection surface-bearing substrate is placed on a ferromagnetic localization means such that the coated surface is not hindered from receiving the test sample. The ferromagnetic localization means is a ferromagnetic material which becomes magnetized in the presence of a magnetic field to attract magnetically responsive particles, and has a characteristic shape, such as wires, spheres or other material providing an irregular or coarse surface when closely packed together. The ferromagnetic material used must have a relatively small area which comes into direct contact with the collection surface-bearing substrate. Additionally, the area of the ferromagnetic localization means which comes into contact with the collection surface-bearing substrate will be in registry with the area on the collection surface on which the target material will become immobilized. Thus, if thin lines of target particles are desired, the corresponding area of the ferromagnetic localization means must be in the form of thin lines. Although ferromagnetic localization means providing thin lines for target particle immobilization is the preferred embodiment, many other shapes or patterns are envisioned to be within the scope of this invention. Some examples include single points; intersecting lines; curved lines; arrays of points, shapes or lines; simple or intricate patterns; and letters, numbers, logos or other indicia. When the ferromagnetic localization means is placed on a magnet and the collection surface bearing substrate is placed on the ferromagnetic localization means, magnetically labelled target particles collected thereon will be immobilized in the pattern or array corresponding to that of the ferromagnetic localization means. Actual magnets could be used in place of the ferromagnetic localization means, but they are less easily formed into the fine shapes contemplated by the present invention. However, it is possible to create the extremely finely focused magnetic field by bringing magnets with opposing poles close together to create high gradients in precisely defined regions of an adjacent collection surface. One such embodiment includes a so called bucking arrangement where in flat magnets (for example, 1 cm×2 cm×0.2 cm thick magnetized through the thickness) are stacked alternately with soft steel of identical dimension. By placing the magnets such that alternating steel segments have magnet poles of the same polarity on each side of the segment, substantial gradients can be achieved which draw the magnetically responsive material to the edges of such arrays. In some cases, the fields created by this arrangement of magnets, rather than magnetic pole pieces, may be preferred, since the magnetic reach is greater, thus allowing the use of thicker collection surface-bearing substrates.

The test sample is placed on the collection surface for a time sufficient for the magnetically labelled target particle to become adhered thereto and for the specific binding pairs to form bonds. With appropriately strong magnetic fields and sufficiently responsive magnetic particles, adherence of the magnetically labelled target particles should occur on the order of thirty seconds. The time required for specific bond formation will depend on the type of specific binding pair used. In the case of antibodies, binding time will depend on the affinity of the antibody and the antigen density. Although diffusion of the target material to the collection surface and specific bond formation theoretically could occur before magnetic adherence, experience has shown that magnetic adherence is generally faster, provided the magnetic field is sufficiently strong. Additionally, magnetic adherence speeds immobilization by bringing the target particle bearing one member of the specific binding pair into close physical proximity to the collection surface coated with the other member of the specific binding pair.

After a time sufficient for magnetic adherence and bond formation, the collection surface-bearing substrate may be removed from the ferromagnetic localization means, and the surface may be washed to remove excess, unbound magnetic material and/or non-target material. The non-target material may be material which was inadvertently trapped in the initial collection, and which due to a lack of specific binding substance is not bound to said surface. The non-target material may also be material which was bound to magnetically responsive particles, but which does not bear the specific binding substance required for immobilization. Optional treatment(s) with additional substances to label or stain the target particles is (are) appropriate at this point. Other sequential reactions involving the target particles may also be performed. It is also possible to subject the target particles to conditions appropriate for the removal of the magnetic label from the target entities. Many such methods are well known to those skilled in the art.

After washing and optional staining steps, the target material will be immobilized on the collection surface for examination. The orderly arrangement of target particles will greatly facilitate their examination. In the case of microscopic examination, less time will be required to scan the microscope slide for the presence of target material. In the case of cells, enumeration, examination and manipulation are possible.

FIG. 1 illustrates a representative apparatus according to this invention, including one embodiment of ferromagnetic localization means. A magnet 1 is shown with a strip of unused, chisel-pointed staples 2 with the chisel points resting upon the magnet 1. A coated microscope cover slip 3 rests on the staple strip 2 awaiting the deposit of the test sample.

Figure 2A:
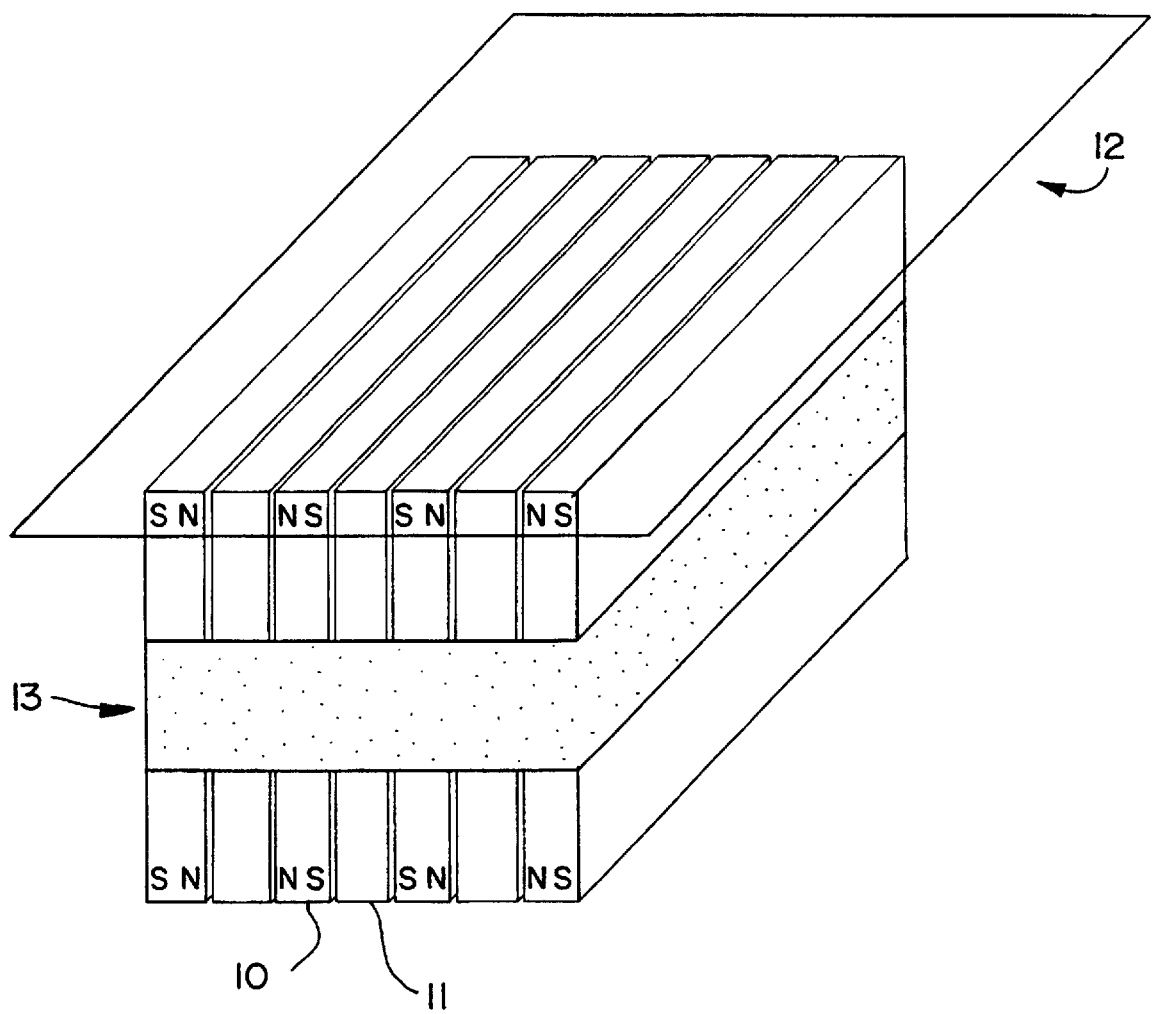
FIG. 2A shows another embodiment of the invention using magnets in a bucking array to provide a ferromagnetic localization means.
Figure 2C:
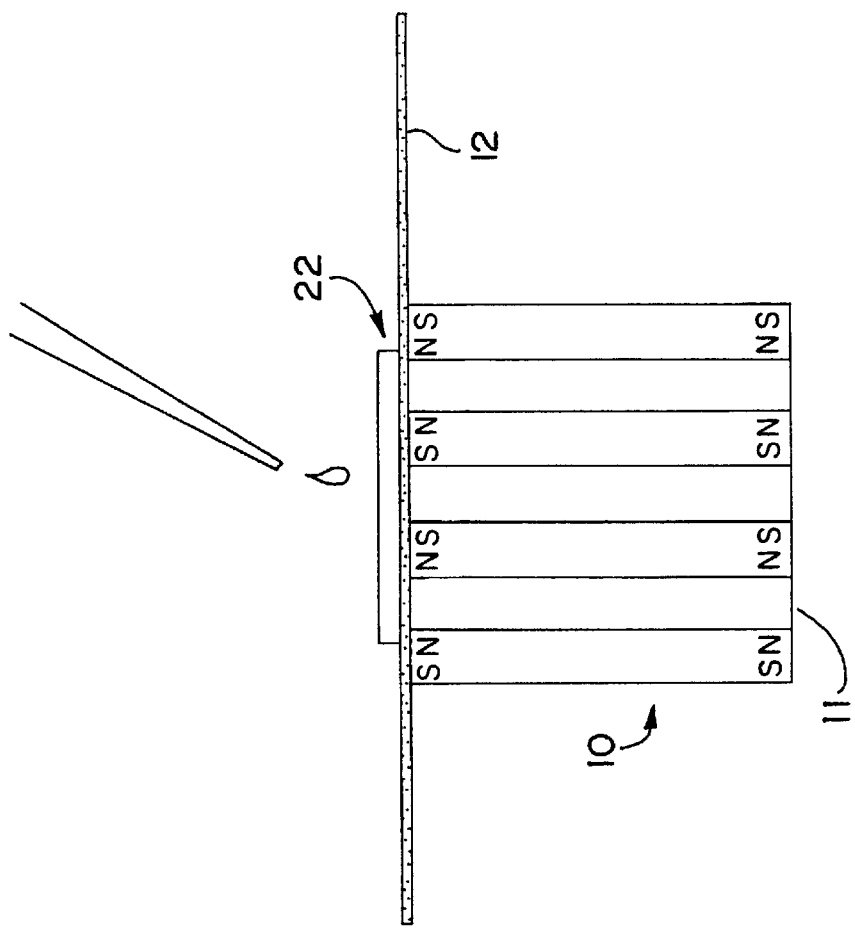
FIG. 2C is a side elevation view of FIG. 2B.
Figure 2B:
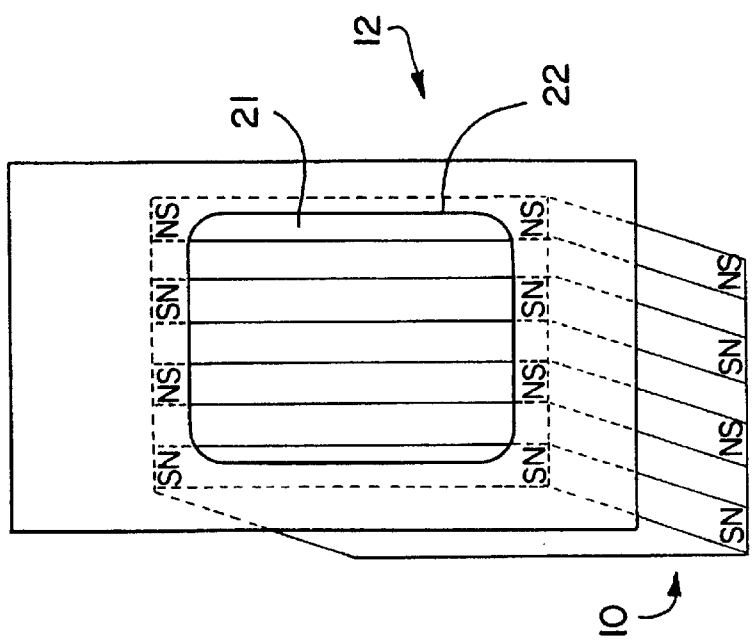
FIG. 2B depicts a top, perspective view of an apparatus for the collection of cells labeled with magnetically responsive material utilizing the "bucking array" of magnets depicted in FIG. 2A.

An alternate embodiment of the invention is illustrated in FIGS. 2A–C. In this instance, magnets 10 are stacked alternately with bars 11 of soft steel which serve as magnetizable spacers. The magnets 10 are assembled with the opposing polarity indicated in the drawing. The magnets and steel spacers are held together by band 13 and thus provide the magnetic field and the ferromagnetic localization means. This assembly can generate a magnetic field gradient in the range of 30–60 K Gauss. The collection surface-bearing substrate 12 shown is intended to represent a microscope cover slip. As can be seen in FIG. 2B, the coverslip 12 rests directly on the ferromagnetic localization means. A non-magnetic, inert gasket 22 is used to contain the liquid test sample on the area of the collection surface in registry with the ferromagnetic localization means for optimal collection. Magnetically labeled cells will collect along lines 21. FIG. 2C shows deposition of a test sample onto the collection surface in the area bounded by gasket 22.

In one embodiment of the invention, a microscope cover slip can be used to collect and immobilize cells for analysis. Preferably, the cells are aligned in a series of parallel lines for easy microscopic examination. Ferromagnetic localization means, such as specially manufactured coarse iron chips with raised, parallel lines can be used. Another ferromagnetic alignment means is a plurality of standard, single-edge razor blades taped securely together with blades exposed and placed on a strong magnet with the blade edges in contact with the collection surface-bearing substrate. A strip of unused staples as illustrated in FIG. 1 is also effective. The cover slip is coated with a cell surface adhesion agent, such as a ligand to a cell-surface receptor such as class I antibody by methods which are well known to those skilled in the art. Thus virtually all cells which come into contact with the coated surface will adhere to it, but any potentially contaminating protein, sera, or nucleic acids or other material which is not of interest can be washed away. In this particular embodiment of the invention, all cells in the specimen material are aligned. The cells are labeled, either directly or indirectly with a magnetic colloid or ferrofluid. Preferably, the labeling is done by direct conjugation of the ferrofluid to a specific binding substance which binds all cells. The specimen material in this embodiment includes cultured cells or cells purified from an original mixture by non-magnetic means. Also included may be a cell mixture which one may desire to analyze in its entirety. An optional concentration step includes centrifugation of the starting cell mixture.

After labeling with the ferrofluid, the cell mixture is placed on the coated collection surface, which is disposed on the ferromagnetic localization means. Alternatively, the cell mixture may be deposited on the collection surface, which is then placed on the ferromagnetic localization means. The magnetically labeled material will collect in registry with the ferromagnetic localization means and the specific binding substance will bind the cells to the surface. Then the cover slip may be removed from the magnet and washed by successively dipping it in wash solutions, including dyes or enzyme substrates. The cover slip is mounted on a microscope slide and examined with a light microscope. The cells are observed in precisely defined parallel lines. With appropriate selection of the ferromagnetic localization means, the lines may be slightly narrower than the field of view of the microscope for the magnification desired. This allows the microscope stage to traverse rapidly up and down along the lines to examine the cells, either manually or mechanically.

In another embodiment of the invention, a microscope cover slip can be used to collect and immobilize subsets of human white blood cells for analysis. The cover slip may be coated with a specific binding substance which binds to a relatively broad subpopulation of cells, for example CD45.

The magnetic colloid or ferrofluid may be directly labeled with an antibody directed toward a characteristic surface antigen of a cell subset of interest, such as CD4 or CD8 (T-lymphocyte cells), CD56 or CD16 (NK cells), CD19 (B-lymphocytes), CD14 (monocytes,) CD83 (dendritic cells), CD33 or CD47 (granulocytes), CD34 (progenitor cells), CD90w (hematopoietic stem cells), CD71 (immature erythrocytes or fetal nucleated erythrocytes), MAb 330 (trophoblasts), EPCAM (epithelial cells), CD31 (endothelial cells), Vimentin (mesenchymal cells) and S-100 (neural cells). In this embodiment of the invention, the specimen material is whole blood, collected by standard venipuncture. An optional initial magnetic separation may be employed to concentrate the original sample and isolate the target cells. The blood is incubated in a test tube with the ferrofluid labeled for a time sufficient for binding of the ferrofluid to the target cells. The test tube is then placed in an external magnetic field, such as described by U.S. Pat. No. 5,186,827. After a collection period sufficient to collect the magnetically labeled cells, the liquid in the tube is aspirated with a pipet. Then the test tube is removed from the magnetic field and the magnetically labelled cells are resuspended in a small amount of buffer. If the starting volume of blood was 5 ml, 200–300 ul of buffer is sufficient to resuspend the target white blood cells. An optional wash and magnetic re-collection to remove excess red blood cells or to aid in the resuspension of the cells is possible before final resuspension into the buffer. After the final resuspension, the entire cell suspension may be placed on the surface of the appropriately coated cover slip which has been placed upon ferromagnetic alignment means as described above. The magnetically labeled material will be localized by the ferromagnetic localization means and the specific binding substance will bind the cells to the collection surface. After removal from the magnetic field and the optional washes, the cover slip is mounted on a microscope slide and examined with a light microscope. The cells are observed in tightly defined parallel lines.

In a further embodiment of the invention, the two magnetic selections may be used to select a distinct subset of cells. The ferrofluid may be coated with an antibody which recognizes one set of cellular determinants, while the coating on the surface recognizes a different set of determinants. For example, a ferrofluid may be coated with CD34 to recognize all progenitor cells, followed by collection and immobilization on a cover slip coated with CD90w, which specifically binds stem cells. In this case, the first selection by ferrofluid labeling is relatively broad and the second selection by surface binding is relatively selective, since the CD90w cells constitute a distinct subset of the CD34 cells. However, it is also possible to select a set of cells which have a set of relatively unrelated determinants. For example, the ferrofluid could be coated with CD4 and the surface could be coated with CD45RO. Thus only cells which are CD4+, CD45RO+ (memory CD4+ T– helper lymphocytes) are collected. In this case, it will be appreciated that the CD4 could be coated on the surface and the CD45RO could be conjugated with the ferrofluid. It is also possible to mix antibodies and to manufacture a ferrofluid with a coating of two or more antibodies. It also may be possible to coat the surface with a mixture of specific binding substances. Any number of combinations of antibodies are possible, depending on the ease of manufacturing a directly coated ferrofluid, ability to coat the substance onto a collection surface, and the usefulness of the selected subset.

In yet another embodiment of the invention would employ an initial analysis and/or separation by flow cytometer. The magnetically labeled target material could be introduced into a flow cytometer after optional magnetic separation of target material as described previously. After flow cytometric analysis of each cell, the magnetically labeled cell could be deposited upon a coated surface which has been placed upon ferromagnetic localization means. The flow cytometric analysis could optionally include fluidic or droplet sorting before deposition upon the coated surface. optionally, the coated surface could include a layer or small "puddles" of liquid to protect against evaporation while droplet sorting. Said liquid could include PBS, culture medium, glycerol or the like. The magnetic gradient induced upon the ferromagnetic localization means would act upon the magnetically responsive target cell to collect and immobilize the cell in a prescribed region of the collection surface, thus allowing for quicker acquisition of the cell after the sample has been analyzed by the flow cytometer. Indexing the cell event on the histogram with the actual cell deposited upon the surface would increase the power of this technology.

In an alternate version of the embodiment of the invention described immediately above, the coated surface could be in constant, processive motion. Thus, a microscope slide having the thickness of a standard cover slip could be used with a ferromagnetic localization means comprising parallel lines or a spiral into or out of the center of the slide. The cells would be aligned in the order of passing through the flow cytometer, thus allowing for indexing of the cell event. Optionally, the coated surface-bearing substrate could be in constant, unidirectional motion, e.g., on a continuous web. Thus, a relatively long coated web could be used to collect and immobilize the target cells therealong, with the collection surface being conveyed past a stationary ferromagnetic localization means, optionally past a washing station(s), and ultimately past an observation station. Thus, the cell event can be observed before the entire sample has been analyzed by the flow cytometer, and the individual cells are easily indexed back to the original histogram. Individual cells are also available for further analysis or manipulation.

Still another embodiment of the instant invention involves aligning a set of cells present in whole blood without an initial magnetic separation step. For example, if one desired to observe the CD4 cells in blood, a sample of whole blood could be incubated with a ferrofluid conjugated to CD4. If a non-magnetic surface were coated with CD3 and placed on a ferromagnetic localization means, then the blood sample may be placed directly on said coated surface. After magnetic collection and immobilization of the target cells and formation of the specific pair bond, the surface could be removed from the magnetic field and washed. Thus, all contaminating cells would be washed away, including platelets and red blood cells.

The disclosures of the following patents and patent applications are incorporated by reference in the present specification, as if set forth herein in full: U.S. Pat. Nos. 4,795,698; 5,200,084; 5,186,827; 5,466,574; 5,512,332; 5,541,072; and 5,597,531; U.S. patent application Ser. Nos. 08/424,271; 08/482,448; 08/482,652; 08/516,694; and No. 60/019,282.

The following examples describe the present invention in further detail and set forth the best mode contemplated by the inventors for carrying out the invention, but are not to be construed as limiting the invention.

EXAMPLE 1

Epithelial Cell Selection from Whole Blood

Colloidal magnetic particles were prepared as described in U.S. patent application Ser. No. 08/482,448. The particles were further conjugated with an antibody which specifically binds to a cell surface protein encoded by the GA73.3-2 gene.

Whole blood was collected from a healthy donor by venipuncture in a 7 ml purple-top Vacutainer® tube. A 5 ml sample of blood was measured with a pipet and placed in an empty 7 ml red-top Vacutainer® tube. 20 µl of cell buffer (isotonic 7 mM sodium phosphate, pH 7.4 with 1% BSA and 50 mM EDTA) containing 125±10 cells from the breast cancer cell line SKBR-3 were added to the blood sample. 2.0 ml of the above-described antibody-conjugated, colloidal magnetic particles was also added to the blood sample and mixed. The final concentration of the magnetic particles was 4.28 µg/ml. The blood sample was allowed to incubate 10–15 min. at room temperature. The Vacutainer tube containing the blood sample was placed in a quadrupole magnetic separation device of the kind described in U.S. Pat. No. 5,186,827. The cavity defined by the four magnets exactly accommodated the dimensions of the tube. The magnetic separation was allowed to proceed for 10 minutes at room temperature. The uncollected material was aspirated and the tube was removed from the quadrupole device. The collected cells were resuspended in 2 ml of cell buffer. The sample container was again placed in the quadrupole device and allowed to separate for 5 minutes. The uncollected material was aspirated and after removal from the quadrupole device, the target cells were resuspended in 150 µl cell buffer.

A 1.9 cm×1.6 cm×5.0 cm magnet (Crucible Magnetics, Elizabethtown, Ky.) was used for the immobilization of the magnetically labeled material. The pole pieces used were a strip of unused standard chisel point staples (Stanley Bostich, East Greenwich, R.I.) A strip of approximately 25 staples were broken off and placed on the magnet, with chisel point touching the magnet. The microscope cover slip was placed so as to overlay the staple strip. The cover slip had previously been coated with an antibody which specifically binds $Her^{2/neu}$. A rubber gasket with an inner area approximately 1.8×1.2 cm was used to contain the sample in registry with the staple strip.

The entire 150 µl sample of resuspended target cells was placed on the area of cover slip bounded by the rubber gasket. The brown-colored ferrofluid could be seen by visual examination to align with the staples, forming approximately 25 brown lines in the clear liquid drop. The cover slip was washed by dipping in PBS to remove the unbound material. The cover slip was air dried and stained with a cytochemical stain (Wright Giemsa.) The cover slip was then mounted on a microscope slide and examined with a light microscope. Fifty-nine of the SKBR-3 cells originally spiked into the blood were observed immobilized in regions corresponding to the ferromagnetic alignment means.

EXAMPLE 2

Selection of CD4 Cells by CD4-Ferrofluid and Immobilization onto Cover Slip Using CD45 MAb In this example, a relatively small subset of target cells was selected using the colloidal magnetic particles and immobilized on a cover slip by means of an additional specific binding pair which binds to the subpopulation of cells comprising the above-mentioned subset. A 0.5 ml sample of whole blood from the purple-top Vacutainer from Example 1 was added to a 12×75 mm polystyrene tube. Added to the blood sample were an aliquot of 0.5 ml of colloidal magnetic particles, prepared as described in Example 1, but conjugated to CD4 Mab, and 20 µl of CD45 MAb-biotin (2 µg), and the sample was incubated for 15 minutes at room temperature. The final concentration of the magnetic particles was 7.5 µg/ml. The tube was then transferred to a quadrupole magnetic separation device, as described in Example 1, and the separation was allowed to proceed for 10 minutes at room temperature. The uncollected material was aspirated and the tube was removed from the device. The collected sample was then resuspended in 1 ml of cell buffer and magnetically separated again, as described herein above, for 5 minutes. The uncollected sample was aspirated and the collected CD4 cells were resuspended in 150 µl of cell buffer. The test sample was deposited on a streptavidin coated cover slip using the same gasket arrangement described in Example 1 and stained. The cells were seen as several lines without any free magnetic particles when observed under a microscope. In this example, all CD4 positive cells were labeled with colloidal magnetic particles and CD45 Mab-biotin and were bound to the cover slip.

What is claimed is:

1. A method for the immobilization of magnetically labelled particulate entities on a collection surface via binding between the members of a specific binding pair, said particulate entities being present in a mixture with at least one non-magnetic substance and comprising one member of a specific binding pair present on the surface of said particulate entities, said method comprising:
   (a) providing a magnetic field;
   (b) disposing said collection surface in said magnetic field, at least a portion of said collection surface, having affixed thereto the other member of said specific binding pair;
   (c) adhering said magnetically labelled particulate entities to said collection surface under the influence of said magnetic field;
   (d) subjecting said adhered magnetically labelled particulate entities to conditions promoting reaction between said specific binding pair members, said particulate entities becoming specifically bound directly to said collection surface, without specific binding between said collection surface and said magnetic label;
   (e) removing said collection surface from said magnetic field; and
   (f) in the absence of said magnetic field, removing any excess magnetically labelled particulate entities and non-magnetic substance present on said collection surface to yield said magnetically labelled particulate entities immobilized on said collection surface.

2. The method as claimed in claim 1, wherein said particulate entity is selected from the group consisting of cells, cell components, bacteria and viruses.

3. The method as claimed in claim 1, wherein said particulate entity is selected from the group consisting of leukocytes, hematopoietic stem cells, T-lymphocytes, NK cells, B-lymphocytes, monocytes, dendritic cells, granulocytes, progenitor cells, erythrocytes, trophoblasts, epithelial cells, endothelial cells, fetal cells, mesenchymal cells and neural cells.

4. The method as claimed in claim 1, wherein said specific binding pair is selected from the group consisting of antibody/receptor, single chain antibody/receptor, protein/receptor, peptide/receptor, nucleic acid/receptor, hapten/anti-hapten, anti-lectin/lectin, biotin/avidin, biotin/streptavidin, lipid intercalating compound/lipid bilayer, and negatively charged cell membrane/positively charged surface.

5. A method for the immobilization of magnetically labelled particulate entities on a collection surface via binding between the members of a specific binding pair, said particulate entities being present in a mixture with at least one non-magnetic substance and comprising one member of a specific binding pair, said method comprising:
   (a) providing a magnetic field-producing means;
   (b) disposing said collection surface in said magnetic field, at least a portion of said collection surface having affixed thereto the other member of said specific binding pair;
   (c) positioning a ferromagnetic localizing means in relation to said magnetic field-producing means and said collection surface such that a magnetic field gradient having a defined pattern is produced on the portion of said collection surface affixing said other specific binding pair member;
   (d) adhering magnetically labelled particulate entities to said collection surface under the influence of said magnetic field gradient;
   (e) subjecting said adhered magnetically labelled particulate entities to conditions promoting reaction between said specific binding pair members; and
   (f) removing any excess magnetically labelled particulate entities and non-magnetic substance present on said collection surface to yield said magnetically labelled particulate entities immobilized on said collection surface in said defined pattern.

6. The method as claimed in claim 5, wherein said particulate entity is selected from the group consisting of cells, cell components, bacteria and viruses.

7. The method as claimed in claim 5, wherein said particulate entity is selected from the group consisting of leukocytes, hematopoietic stem cells, T-lymphocytes, NK cells, B-lymphocytes, monocytes, dendritic cells, granulocytes, progenitor cells, erythrocytes, trophoblasts, epithelial cells, endothelial cells and fetal cells.

8. The method as claimed in claim 5, wherein said specific binding pair is selected from the group consisting of antibody/receptor, single chain antibody/receptor, protein/receptor, peptide/receptor, nucleic acid/receptor, hapten/anti-hapten, anti-lectin/lectin, biotin/avidin, biotin/streptavidin, lipid intercalating compound/lipid bilayer, and negatively charged cell membrane/positively charged surface.

9. The method as claimed in claim 5, further including analyzing said immobilized particulate entities by microscopy.

10. The method as claimed in claim 5, further including analyzing said immobilized particulate entities by fluorescence cytochemistry.

11. The method as claimed in claim 5, further including analyzing said immobilized particulate entities by immunocytochemistry.

12. Apparatus for immobilization of magnetically labelled particulate entities on a collection surface via binding between the members of a specific binding pair, said particulate entities comprising one member of said specific binding pair, said apparatus comprising:
   (a) a magnetic means for providing a magnetic field; and
   (b) a collection surface disposed in the magnetic field generated by said magnetic means, at least a portion of said collection surface having affixed thereto the other member of said specific binding pair; and
   (c) a ferromagnetic localization means which is separate from said magnetic means that provides a magnetic field and which is operably associated with said collection surface in said magnetic field for producing a magnetic field gradient having a defined pattern on the portion of said collection surface affixing said other specific binding pair member, whereby said magnetically labelled particulate entities are caused to adhere to said collection surface under the influence of said magnetic field gradient and to become immobilized on said collection surface when subjected to conditions promoting reaction between said specific binding pair members.

13. The apparatus as claimed in claim 12, wherein said ferromagnetic localization means comprises a series of ferromagnetic strips positioned in closely-spaced parallel array within said field.

14. The apparatus as claimed in claim 12, wherein said magnetic means comprises a series of magnetic poles and said ferromagnetic localization means comprises a series of elongated magnetizable spacers disposed between said poles.

* * * * *